United States Patent [19]

Bhutani

[11] Patent Number: 4,684,516
[45] Date of Patent: Aug. 4, 1987

[54] SUSTAINED RELEASE TABLETS AND METHOD OF MAKING SAME

[75] Inventor: Baldev R. Bhutani, Libertyville, Ill.

[73] Assignee: Alra Laboratories, Inc., Gurnee, Ill.

[21] Appl. No.: 735,046

[22] Filed: May 17, 1985

Related U.S. Application Data

[63] Continuation-in-part of Ser. No. 518,923, Aug. 1, 1983, abandoned.

[51] Int. Cl.$^4$ .............................................. A61J 3/02
[52] U.S. Cl. ....................................... 424/19; 427/3; 264/123; 264/109
[58] Field of Search ................... 427/3; 424/19–21; 264/123, 109

[56] References Cited

U.S. PATENT DOCUMENTS 2,798,838 7/1957 Robinson ............................. 424/35
3,907,983 9/1975 Seth ....................................... 424/35

FOREIGN PATENT DOCUMENTS 1390032 8/1971 United Kingdom .
1287431 8/1972 United Kingdom .

*Primary Examiner*—Sam Scluenberg
*Attorney, Agent, or Firm*—Leydig, Voit & Mayer

[57] ABSTRACT

This invention relates to new dosage units of medicinal agents for oral administration in the form of tablets which provide a controlled rate of release of the medicament in the gastrointestinal tract. More particularly, the invention relates to dense compressed tablets comprising mainly sustained release coated pellets processed such that the tablets disintegrate rapidly in aqueous and gastric fluids at body temperature, releasing the medicinal agent contained therein gradually over a relatively long period of time.

20 Claims, 6 Drawing Figures

SUSTAINED RELEASE TABLETS AND METHOD OF MAKING SAME

This application is a continuation-in-part of Ser. No. 518,923 filed Aug. 1, 1983, now abandoned.

This invention relates to a new dosage units of medicinal agents for oral administration in the form of tablets which provide a controlled rate of release of the medicament in the gastrointestinal tract. More particularly, the invention relates to dense compressed tablets comprising mainly coated pellets processed such that the tablets disintegrate rapidly in aqueous and gastric fluids at body temperature. Specially coated pellets are formulated with disintegrants so that they hydrate quickly disintegrating the tablets in a short time to release the medicinal agent contained therein gradually over a relatively long period of time.

This invention also relates to the method of making such coated pellets which can be compressed into a tablet or pill of any size or shape.

BACKGROUND OF THE INVENTION

The importance of providing dosage unit forms of medicinal agents for oral administration which release the drug slowly and at a uniform rate has long been recognized and has become more apparent as new drugs are made available. If the medicament is released too quickly, the stomach may become upset and the acid environment may have an adverse effect upon the drug. Sometimes the too rapid absorption of large amounts of potent drugs results in unnecessarily high blood levels of the drug which may, in turn, result in unpleasant side-effects or even toxic manifestations.

To ensure a controlled, long-lasting, continuous and not too intensive effective action of a therapeutic agent in the human body, it is necessary to be able to delay the absorption of the therapeutic agent by the body. This is especially important for water-soluble medicinal agents which are normally absorbed by the body fluids immediately after administration and consequently produce normally only a very short duration of effective action.

Many drugs such as potassium chloride for hypokalemia, aspirin, acetaminophen and ibuprofen for rheumatism, nicotinic acid for hypercholesteremia, theophyllin for the relief of bronchial asthma, griseofulvin for the treatment of conjunctivitis, corneal ulcer and antibiotics for fighting bacterial and viral infections, function best by maintaining the concentration of the medicament at the optimum therapeutic blood level. The traditional method of taking a capsule every few hours is often inconvenient and results in non-compliance by the patients.

As one example for the need for a dosage unit form which releases the drug at a relatively constant rate over a longer period of time, reference may be made to the treatment of hypokalemia with potassium salts such as potassium chloride, potassium bicarbonate, potassium citrate and potassium glycolate and others. In this treatment, relatively large amounts of potassium salts are given orally, often resulting in unpleasant side effects such as gastric ulceration, occasional bleeding and others. Analgesics and antiarthritic drugs when taken in large doses often give rise to similar undesirable side effects. Single smaller doses of antibiotics and antibacterial agents taken to fight infections have the desired therapeutic effect for no more than a few hours whereas large doses tend to result in severe abdominal cramping, upset stomach, vomiting, nausea, diarrhea and occasional hepatic dysfunction.

Up to now one of the methods commonly used in an attempt to provide prolonged duration of therapeutic agent is to mix the agent with insert waxy materials, e.g., calcium, magnesium and aluminium soap salts and/or other insoluble or partially soluble materials. This mass is then granulated using aqueous or non-aqueous solvents to provide granules, which are then compressed into tablets or pills. The sustained release effect is achieved when the tablet erodes or dissolves gradually in the gastrointestinal tract. This method is exemplified in U.S. Pat. Nos. 2,793,979, 3,065,143, 3,102,845, 3,184,386, 3,437,726 and 3,558,768.

The dosage form described above has a big disadvantage in that the tablet or pill travels through the intestinal tract as one large mass constantly in physical contact with gastrointestinal tissue, thereby causing intestinal and gastric ulceration, occasional bleeding and other undesirable side effects such as nausea, vomiting, epigastric distress and oval thrush.

Another commonly employed method for obtaining a so-called "prolonged" therapeutic effect from a pharmaceutical formulation is to coat a drug onto an innocuous core, e.g., nonpareil seeds (tiny sugar pellets) or onto drug crystals themselves. The thus coated drug pellets are then over-coated with several layers of retarding waxes or insoluble mixes in such fashion that, when filled into gelatin capsules, the release of the active drug from the capsule during its passage through the stomach and intestinal tract, is even and gradual. This method is exemplified in U.S. Pat. Nos. 3,383,283, 2,921,883, 3,365,365, 3,220,925 and 3,119,742.

Such a sustained release dosage form is limited, however, by the amount of coated beads or pellets that can be put into a size capsule that is convenient for swallowing. For example, a #1 hard gelatin capsule holds approximately 400 mg. of finished sustained release pellets and a #0 size capsule approximately 600 mg.

An examination of other prior art reveals numerous attempts to solve the problems defined above, with only limited success. None of the noted prior art employs my new inventive process and solution of the problem. For example, Press U.S. Pat. No. 2,953,497 describes a basic timed release composition and a method of preparing such composition. The patent describes therapeutically active ingredients which are coated on or mixed with a sugar/corn starch mixture to form granules. The therapeutically active ingredient-containing or coated granules are thereafter coated with shellac and/or a cellulose acetate phthalate solution to reduce the rate of release of the therapeutically active ingredient. The patent does not disclose my method of forming a tablet containing disintegrant-coated medicament-containing controlled release particles or such a tablet itself.

Barry U.S. Pat. No. 2,996,431 is directed to a procedure for making a friable tablet and the tablet produced thereby. According to the patent, the tablet can be broken into small sized particles by application of the pressure of the thumb or other finger on the tablet against a surface, such as that of a table, in a single operation. The tablet is composed of granules or spheroidal pellets composed of sugar/corn starch with a coating of medicinal agent. The medicinal agent-containing pellets are then coated with, inter alia, shellac or cellulose esters, such as the acetate and acetate phthalate. The granules or pellets are then incorporated in a matrix or binder and pressed into the desired shape. The patent does not describe my use of a thin, uniform coating of a disintegrant on a medicament containing pellet, nor my process of forming a compressed tablet containing such disintegrant-coated pellets.

Halley U.S. Pat. No. 3,044,938 describes a sustained action pharmaceutical tablet and a process of making the same. The disclosure indicates that at least some portions of a medicament incorporate an ingredient which simultaneously functions as an "action-retardant" and as a binder. By including a plurality of such special action-retarding and binding ingredients into the same tablet or by incorporating action-retarding and binding ingredients and medicament in unaltered form, sustained-release action may be obtained. The patent does not, however, describe my process, or a tablet formed thereby, in which retarded or coated pellets of medicament are further coated with a layer of disintegrants prior to compressing the tablet.

Hermelin U.S. Pat. No. 3,115,441 discloses timed release tablets in which a plurality of small particles of an analgesic drug coated with a solution-resistant coating is dispersed throughout a compressed matrix including particles of the same analgesic drug in uncoated form. There is no discussion in the patent of my use of disintegrants, nor of my process for forming disintegrant-coated medicament-containing particles in a compressed tablet.

Berger U.S. Pat. No. 3,344,029 describes a sustained release preparation which includes a plurality of resilient cores, each of which is formed from a cohesive intimate mixture of finely divided, therapeutically active material in powder form and an ingestible material which is resistant to disintegration in the gastrointestinal tract. A portion of the core is coated with alternating coatings of therapeutically active materials and ingestible material. The patent does not disclose the use of a disintegrant layer on a sustained release medicament-containing particle, nor a compressed tablet including a plurality of such disintegrant-coated particles, as my invention describes.

Noyes U.S. Pat. No. 536,155, Mori et al. Japanese Patent Publication No. 53-127,821, and Wilen U.S. Pat. No. 2,297,599 disclose various forms of coated particles of medicament but they do not describe my uniform coating of a retarding material on a medicament-containing particle overlaid with a uniform coating of disintegrant material and then compressed into a dense tablet that breaks up quickly in the body.

SUMMARY OF THE INVENTION

I have now found a unique composition, as described in the present invention, which provides a dosage unit form for the controlled administration of medicaments which releases the medicament at a relatively uniform rate over a sustained period of time. This dosage unit form not only avoids the above-mentioned difficulties, but provides various advantages in addition thereto. For instance, the equivalent of two or three normal doses of a drug in the form of coated pellets may be incorporated into one tablet which may be taken only once every eight to twelve hours. Thus, it is possible to maintain the action of the drug during the night while the patient is asleep as well as during the day when he may find it inconvenient to take frequent doses of medication. Furthermore, since the tablets rapidly disintegrate, releasing the individual coated pellets, the gastric residence time of the dosage form is significantly reduced, thereby minimizing the side effects.

Another advantage with the present invention is that the compressed tablet can be bisected on upper, or lower, or both sides of the tablets which make it easier to administer one-half tablet or one-half dose, something which is impossible when coated pellets are dispensed in gelatin capsules.

According to the invention, sustained release tablets or pills may now be prepared which do not exhibit the shortcomings enumerated above and which may contain relatively large amounts of active ingredients. Thus, according to the present invention, the active ingredient is first coated onto non-pareil beads or onto drug crystals or granules. These pellets are then divided into several groups and varying amounts of retarding materials are applied to different groups. Upon subsequent mixing of the groups, the combined effect of the total pellets will provide gradual release of the medicine. These pellets are then cured in the oven to stabilize the release rates.

The stabilized pellets are then coated with several layers of disintegrating agent or agents and compressed into tablets or pills, after adding a small amount of lubricants or other inert ingredients, if necessary. Such a compressed tablet, when tested in water or gastric gluid, breaks up quickly thereby releasing the individual pellets in a matter of minutes, whereupon they act as independent pellets releasing their medicine at a predetermined rate.

By following this method of preparing a drug, a relatively large amount of the drug can be compressed into a tablet size which is still easy to swallow. As much as 1500 mg. of the drug can now be administered in a tablet size which is no bigger than #0 size gelatin capsule. In brief, this process results in a tablet containing approximately 200% to 250% the amount of medicament that could be placed into a capsule of equal size. My tablets will significantly reduce the gastric residence time, thus eliminating most, if not all, of the gastric related side effects because the smaller size pellets pass through the pyloric valve swiftly. The non-disintegrating type tablets, especially sizes bigger than 7/16" to ½" diameter pass through the pyloric valve with difficulty.

The claimed invention, distinguishable not only on the basis of the method of forming the tablet but the tablet itself, may be further distinguished from the prior art based on the effects achieved by the claimed tablet. Whereas the prior art incorporates disintegrants into a tablet or a capsule simply by mixing the disintegrants with coated beads and granules and thereafter compressing the mixture when a tablet is formed, the present invention coats the disintegrant onto a pellet and thereafter compresses a plurality of the disintegrant-coated pellets into tablet form. The claimed process and product formed thereby, which include medicament-containing pellets uniformly coated with disintegrant, provide very reliable and predictable disintegration times for the tablet. This permits more accurate determination of dosages and intervals between release of medicament.

Another effect which is obtainable by the tablets of the present invention is to reduce the gastric residence time. Thus, a tablet according to the present invention can be made which will disintegrate rapidly in the stomach into coated beads. These beads, being small in size, move rapidly into the intestine, thereby reducing the gastric residence time of the medicament significantly and the concomitant gastric irritation associated with many drugs, such as aspirin, ibuprofen, potassium chloride, antibiotics, etc.

The tablets of the present invention permit the administration of larger, single doses. As distinguished from prior art tablets in which the disintegrant is mixed with the medicament-containing beads, the present invention is more efficient in that it allows smaller amounts of disintegrant to be used by providing a thin, uniform coating of the disintegrant on the medicament-containing bead. Since a smaller portion of the volume of the compressed tablet of the present invention is occupied by disintegrant, as compared to compressed mixtures of the prior art, a greater amount of medicament may be incorporated in the same volume tablet. Thus, the present invention permits the administration of about 1,200 to about 1,600 mg. of medicated beads in a single dose without effecting the rate of release of medication as compared to not more than about 600 to 700 mg. of medicated beads in a single dose prepared according to the prior art.

The present invention permits a greater uniformity in effect as a result of a greater uniformity of coating of the disintegrant, as compared to mixing disintegrant with medicament-containing beads. Generally, the disintegrants are of a much smaller size (100 to 300 mesh) compared to the coated medicaments which are generally about 10 to 15 times larger (10 to 20 mesh). As a result, when simply mixed together, the large and small particles tend to separate with the small particles settling on the bottom of a container and being nonuniformly dispersed in the mixture. Thus, the rates of disintegration may differ for the "mixed" tablet, not only from one tablet to the next, but also as compared to what may be obtained according to the tablets of the present invention.

DETAILED DESCRIPTION OF THE INVENTION

In one embodiment of this invention, the tablet composed of 85% to 98% of the drug-containing, coated, spherical pellets, the remainder being composed of binder and lubricants, preferably between 90% to 100% of the tablet. The pellets are predominantly of a size ranging from 12 to 30 mesh, with sizes 16 thru 24 mesh being preferred and they all may be the same size or of different sizes within that range.

The spherical drug pellets may be coated using conventional coatings to simply retard the release rate of the medicament, or they may be enteric coated so that they will not release the drug in the intestines. The coating materials used may also be such that the coated pellets will release the drug at selected locations within the gastrointestinal tract. This result can be achieved by using specific enzymes or specific chemicals which interact with the enzymes present or dissolve at the prevailing pH within the gastrointestinal tract.

A compressed tablet prepared using the above-mentioned technique may contain only a single drug component or it may contain different pellets containing different drugs, which are mixed together before compressing into tablets. A mixture of different pellets of different drugs coated differently, i.e., wax retarded, enteric coated and site specific coated will provide a tablet which is capable of providing more than one medicament at several locations within the gastrointestinal tract at a controlled specific release rate for each medicament.

The film coating material may be applied by any procedure which achieves a continuous film of essentially uniform thickness. One method of film coating involves rotating a bed of uncoated beads (e.g., nonpareil) in a conventional tablet coating pan and applying a solution or dispersion of the coating agent in a suitable solvent by pouring or spraying onto the moving beads, care being taken to uniformly coat each bead and to avoid incomplete film coating such as is caused by bead agglomeration, etc. Drying of the coated beads is accomplished by exposure to warm, dry air. The coating procedure conveniently is continued until the desired film thickness is obtained. The resulting film coated beads are then cured if necessary with heat (air drying, baking or force drying), polished and finished as desired. Other coating procedures such as fluid bed coating, vertical spray coating, etc., can also be employed.

Although my novel formulation is peculiarly adapted to the use of "water soluble" medicaments, it may be readily modified to include "water insoluble" therapeutics, singly, in combination with each other, or in combination with water soluble medicaments, and it is intended that this modification be included within the scope of the present invention. Inasmuch as a water insoluble drug can be made available for absorption from the intestinal tract only by being directly exposed to the intestinal mucosa, such exposure can be accomplished by incorporating in the formulation an appropriate amount of hydrophilic gum. The quantity of the hydrophilic gum should be such that the pellets erode slowly while traveling through the intestinal tract, thereby rendering the water insoluble drug available for absorption.

For a more detailed explanation of the invention, reference is made to FIGS. 1-6.

Figure 1:
FIG. 1 represents, in enlarged form, a pellet 10 graphically as a sphere although in reality not all are perfect spheres but rather a variety of spheroidal forms.
Figure 2:
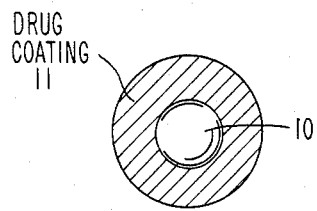
FIG. 2 represents the pellet 10 to which a medicament 11 has been applied by coating. The medicament is exemplified as continuous and uniform in thickness, but in reality the medicament may be deposited in somewhat less than complete uniformity.
Figure 3:
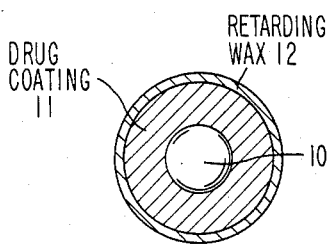
FIG. 3 represents the pellet after one or more coating applications 12 of retarding wax such as stearic acid, carnauba wax or a mixture thereof are applied. The coating 12, if desired at all, is deposited as described above over the surface of the medicated pellet.
Figure 4:
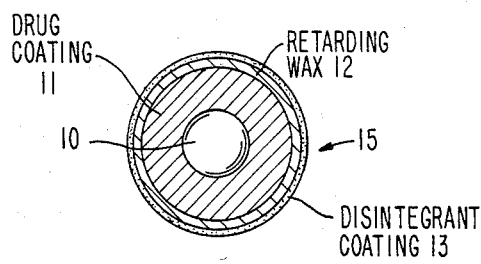

FIG. 4 represents the pellet 15 after applications of a coating of disintegrant materials 13 over the retarding wax 12 shown.

Figure 5:
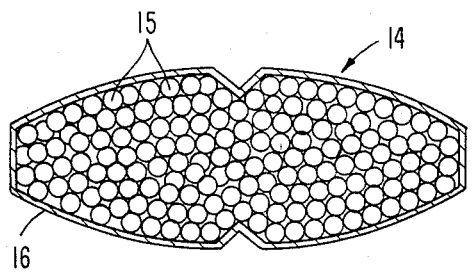

FIG. 5 represents an enlarged cross-section of a compressed tablet 14 consisting of the coated pellets 15 exemplified in FIG. 4. The spheroidal pellets 15 are actually somewhat flattened by the compression force of the tablet press during tabletting, but due to the nature of the coating materials and the layer of disintegrants, the integrity of the retarding coating is essentially maintained. The exterior surface of the tablet 16 is not an applied coating as such, but is exemplified herein to show the hard compressed surface area which results from the force of the tablet press on the pellets 15.

Figure 6:
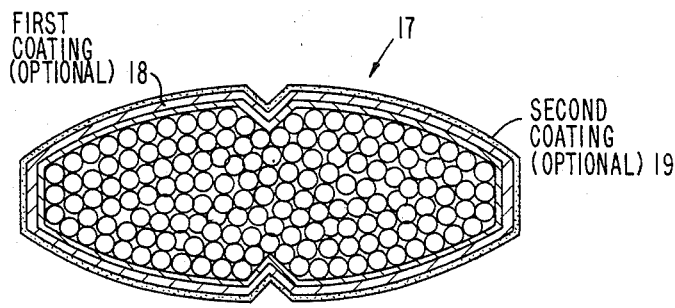

FIG. 6 shows an enlarged cross-section of the tablet 14 after application of finish coatings to make a coated tablet 17. Depicted here are two layers of coating materials, 18 and 19. This number could be zero to four depending upon the need to coat the tablet or the type of coating applied.

The nature of the coating of my invention will vary from pellet to pellet within the same batch, as well as in uniformity and thickness, as is known to persons skilled in this art. Some pellets will have more direct and continuous layers formed by the orientation of the powder particles than other pellets and the same disintegrants may create weak spots in the coating of some pellets but not in others.

The overall effect, however, is as stated more fully herein, and reproducibility can be obtained from batch to batch and from samples within a batch.

The rate of release of medicament from a particular dose can be controlled by:

(a) Varying the relative solubility of the drug;
(b) Varying the drug concentration per pellet;
(c) Varying the number of pellets (population) per unit dose;
(d) Varying the thickness of the coating;
(e) Varying the amount and ratio of retarding wax;
(f) Varying the characteristics of the fatty acids used in retarding wax;
(g) Blending two or more batches of pellets with different release rates;
(h) The amount and type of disintegrants used.

Because the present method for providing sustained release dosage units and the compositions produced thereby are not limited by the physical or chemical properties of the drugs utilized, a large number of drugs of various physical and chemical properties may be embodied therein. Without intending to exclude any useful pharmaceutical, the following is a list of representative pharmaceuticals or drugs by generic or chemical name which may be used to prepare sustained release dosages according to the present invention:

| Analgesic or Antipyretic Agents |  |
| --- | --- |
| Aspirin | |
| Acetaminophen | |
| Salsalate | |
| Antibiotics/Antibacterial Agents/Vermicidal Agents | |
| Penicillin | Griseofulvin |
| Tetracycline | Dicloxacillin Sodium |
| Chlortetracycline | Erythromycin and its salts |
| Oxytetracycline | Piperazine Citrate & |
| Neomycin | Hexahydrate |
| Chloramphenicol | Methanamine Hippurate & |
| Cephradine | Mandalate Salts |
| Nalidixic Acid | Sulfasoxizole and other |
| Cephloseporins | Sulfonamide Salts |
| Antiepileptic Agents | |
| Ethotoin (Peganone) | |
| Trimethadione (Tridione) | |
| Phenytoin | |
| Paramethadione (Paradione) | |
| Sodium Valproate | |
| Sodium Hydrogen Valproate | |
| Dietary Supplements | |
| Nicotinic Acid | |
| Ferrous Sulfate and other Fe Salts | |
| Urinary Acidifiers & Alkalizers | |
| Potassium Acid Phosphate | |
| Sodium Acid Phosphate | |
| Potassium Acetate | |
| Bronchodilators/Vasodilators | |
| Theophyllin | |
| Oxytriphylline | |
| Potassium Supplements | |
| Potassium Chloride | |
| Potassium Citrate | |
| Potassium Gluconate | |
| Potassium Bicarbonate | |
| Sedatives and Hypnotics | |
| Pentabarbital | Carbromal |

| -continued | |
| --- | --- |
| Phenobarbital | Barbital |
| Secobarbital | Amobarbital |
| Codeine | Butabarbital |
| Bromisovalum | Methocarbamol |
| Sulfonamides | |
| Sulfamethoxydiazine | |
| Sulfaethiodole | |
| Sulfasoxizole & other | |
| Sulfonamide Salts | |
| Cardiovascular Drugs | |
| Papaverine Hydrochloride | |
| Anti-Inflammatory/Antiarthritis Drugs | |
| Diflunisal | |
| Ibuprofen | |
| Indocin | |
| Procainamide Hcl | |
| Anti-Parkinson's Disease | |
| Levo-Dopa | |

The disintegrating or swelling agents which may be according to the invention are substances which by capillary action or by process of hydration upon contact with water help in disintegrating the compressed tablet into individual pellets. Specific examples of such swelling agents, which may be used alone or in any suitable mixture with other members of the group, are the following: Various starches, such as corn starch, potato starch, rice starch, sodium carboxymethyl starches, pregelatinized starches, sodium starch glycolate, cellulose powder and cellulose ethers, such as carboxymethyl cellulose (CMC), methylcellulose, hydroxymethyl cellulose, polyacrylic acid (Carbopol 934), sodium alginate and alginic acid, plantago ovata seed husk, modified cellulose gums (AcDisol) and pectin. Particularly preferred are sodium carboxymethyl starches, pregelatinized starches and corn starch or combination of above starches with cellulose ethers. The disintegrant component is employed in amounts between about 2 percent to about 15 percent by weight of the tablet, preferrably between about 5 percent to 10 percent by weight.

The well known water-insoluble polymers may be employed, a preferred polymer being a polyvinylacetate of medium viscosity.

Another method of preparing a rapidly disintegrating tablet made up of coated beads employs an effervescent mixture, whereby approximately one-half of the beads are coated with sodium bicarbonate, potassium bicarbonate or similar salts and the other half with organic acids, such as citric acid, tartaric acid or both. A compressed tablet consisting of such beads in contact with water or gastric fluids will generate effervescent action and disintegrate the tablet into beads.

There is no restriction on the inclusion of other commonly employed excipients in the formulation of the novel combination of this invention. Thus, one may employ as diluents, in whatever quantities are indicated, such components as dibasic calcium phosphate, lactose, mannitol and others. One may also include as binders, to ensure additional cohesive properties over and above those exerted by P.V.P., such gums as acacia or tragacanth.

EXAMPLE NO. 1

Nonpareil seed (sugar pellets), 20.0 kg., all passing through a No. 30 U.S. mesh screen, 90% passing through a No. 35 U.S. mesh screen, and not over 10% passing through a No. 40 U.S. mesh screen are placed in a 48-inch coating pan. The pan is set in rotation and coating solution is sprayed slowly onto the pellets in order to wet them evenly. Then 400 gm. of Potassium Chloride powder, containing 5% talcum powder, are sprinkled on the wetted mass of nonpareil seeds. The pellets are dried in warm air. The addition of the coating solution, coating powder and the drying procedure are repeated to apply additional coats until all the Potassium Chloride powder is used up. Two final coatings are added, each coat consisting of coating solution followed by talcum powder. The pellets are thoroughly dried and screened through a No. 12 mesh screen and on a No. 20 mesh screen.

The screened pellets are divided into three equal parts and returned to three separate coating pans and coated with coating solution followed by dusting with a mixture of stearic acid, carnauba wax and talc which work as retarding wax. The pellets in the first pan are thus coated with 3.3 kg. of retarding wax, the second pan with 4.95 kg. of the retarding wax and the third with 6.6 kg. of retarding wax. All three groups are thoroughly dried. The medicament release rate of each group is checked and then the three groups are mixed together and the whole is divided into two sections and each is returned to a separate coating pan.

Now the coating solution is sprayed into each pan, followed by dusting of a mixture of corn starch and sodium starch glycolate (disintegrant). This process is continued until 6% w/w of the disintegrant has been added. The pellets are thoroughly dried, and screened through a 12 mesh screen and onto a 30 mesh screen. These pellets are then compressed on a tablet press to a weight which provides 750 mg. of Potassium Chloride per tablet.

These tablets are then film-coated using conventional coating techniques for improving appearance and acceptability.

The coated tablets thus obtained released the active ingredient at a sustained rate over a period of six to seven hours under simulated physiological conditions.

The disintegration time of these tablets was determined by U.S.P. method using the Stoll-Gershberg apparatus. Six tablets were placed in the basket of the apparatus, and the basket was lowered into an 1000 ml. beaker containing 900 ml. simulated gastric fluid maintained at 37° C. The apparatus was then operated in the prescribed manner.

EXAMPLE NO. 2

Potassium Chloride Granules, 40.0 kg., all passing through a No. 20 U.S. mesh screen, 90% passing through a No. 30 mesh screen, and not over 10% passing through a No. 40 U.S. mesh screen are placed in a 48-inch coating pan. The pan is set in rotation and coating solution is sprayed slowly onto the pellets in order to wet them evenly. Then 400 gm. of Potassium Chloride powder containing 5% povidone powder are sprinkled on the wetted mass of nonpareil seeds. The pellets are dried in warm air. The addition of the coating solution, and coating powder and the drying procedure are repeated to apply additional coats until all the Potassium Chloride powder is used up. Two final coatings are added, each coat consisting of coating solution followed by talcum powder. The pellets are thoroughly dried and screened through a No. 16 mesh screen and on a No. 30 mesh screen. The yield is approximately 100 kg.

The screened pellets are divided into three equal parts and returned to three separate coating pans and coated with coating solution followed by dusting with a mixture of stearic acid, carnauba wax and talc which work as retarding wax. The first pan is thus coated with 3.3 kg. of retarding wax, the second pan with 4.95 kg. of the retarding wax and the third with 6.6 kg. of retarding wax. All three parts are thoroughly dried. The release rate of each part is checked and the three parts are mixed together and again divided into two sections and returned to the coating pans.

Now the coating solution is sprayed onto each pan, followed by dusting of mixture of alginic acid and sodium carboxymethyl starch (disintegrant). This process is continued until 10% w/w of the disintegrant has been added. The pellets are thoroughly dried, and screened through a 12 mesh screen and onto a 30 mesh screen. The yield is approximately 125 kg. These pellets are then compressed on a tablet press at a weight which is equal to 750 mg. of Potassium Chloride per tablet.

These tablets are then film-coated using conventional coating techniques for improving appearance and acceptability. The coated tablets thus obtained released the active ingredient at a sustained rate over a period of six to seven hours under simulated physiological conditions.

EXAMPLE NO. 3

Nonpareil seed (sugar pellets), 20.0 kg., all passing through a No. 30 U.S. mesh screen, 90% passing through a No. 35 mesh screen, and not over 10%, passing through a No. 40 U.S. mesh screen are placed in a 48-inch coating pan. The pan is set in rotation and coating solution is sprayed slowly onto the pellets in order to wet them evenly. Then 400 gm. of aspirin powder containing 5% talcum powder are sprinkled on the wetted mass of nonpareil seeds. The pellets are dried on warm air. The addition of the coating solution, and coating powder and the drying procedure are repeated to apply additional coats until all aspirin powder is used up. The final coatings are added, each coat consisting of coating solution followed by talcum powder. The pellets are thoroughly dried and screened through a No. 12 mesh screen and on a No. 20 mesh screen. The yield is approximately 100 kg.

The screened pellets are divided into three equal parts and returned to three separate coating pans and coated with coating solution followed by dusting with a mixture of stearic acid, carnauba wax and talc which work as retarding wax. The first pan is thus coated with 3.3 kg. of retarding wax, the second pan with 4.95 kg. of the retarding wax and the third with 6.6 kg. of retarding wax. All three parts are thoroughly dried. The release rate of each part is checked and the three parts are mixed together and again divided into two sections and returned to the coating pans.

Now the coating solution is sprayed onto each pan followed by dusting of mixture of potato starch and modified cellulose gum (AcDisol) (disintegrant). This process is continued until, 8% w/w of the disintegrant has been added. The pellets are thoroughly dried, and screened through a 12 mesh screen and onto a 30 mesh screen. The yield is approximately 125 kg. These pellets are then compressed on a tablet press at a weight which is equal to 1000 mg. of Aspirin per tablet.

The tablets thus obtained released the active ingredients at a sustained rate over a period of six to eight hours under physiological conditions.

EXAMPLE NO. 4

Nonpareil seed (sugar pellets), 30.0 kg., all passing through a No. 30 U.S. mesh screen, 90% passing through a No. 35 U.S. mesh screen, and not over 10% passing through a No. 40 U.S. mesh screen are placed in a 48-inch coating pan. The pan is set in rotation and coating solution is sprayed slowly onto the pellets in order to wet them evenly. Then 400 gm. of theophyllin anhydrous containing approximately 5% talcum powder are sprinkled on the wetted mass of nonpareil seeds. The pellets are dried in warm air. The addition of the coating solution, coating powder and the drying procedure are repeated to apply additional coats until all the theophyllin anhydrous powder is used up. Two final coatings are added, each coat consisting of coating solution followed by talcum powder. The pellets are thoroughly dried and screened through a No. 12 mesh screen and on a No. 20 mesh screen. The yield is approximately 100 kg.

The screened pellets are divided into three equal parts and returned to three separate coating pans and coated with coating solution. The coating solution may be a solution or dispersion of methyl cellulose, ethyl cellulose or a mixture thereof in a solvent system such as a water-ethanol mixture, an ethanol-methylene chloride mixture or a methanol-methylene chloride mixture. The first pan is thus coated with 8% by weight, the second pan with 10% by weight and the third with 12% by weight of the dry solids from the aforesaid solution. All three parts are thoroughly dried. The release rate of each part is checked and the three parts are mixed together and again divided into two sections and returned to the coating pans.

Now the coating solution is sprayed onto each pan, followed by dusting mixtures of corn starch and cellulose powder (Solka Flog) (disintegrant). This process is continued until 10% w/w of the disintegrant has been added. The pellets are thoroughly dried, and screened through a 12 mesh screen and onto a 30 mesh screen. The yield is approximately 125 kg. These pellets are then compressed on a tablet press at a weight which is equal to 450 mg. of theophyllin anhydrous per tablet.

These tablets are then coated using conventional coating techniques for improving appearance and acceptability. The coated tablets thus obtained released the active ingredient at a sustained rate over a period of 10 to 12 hours under physiological conditions.

EXAMPLE NO. 5

Ibuprofen granules 40 kg. all passing through a No. 20 U.S. mesh screen, 90% passing through a No. 30 mesh screen, and not over 10% passing through a No. 50 U.S. mesh screen are placed in a 48-inch coating pan. The pan is set in rotation and coating solution is sprayed slowly onto the pellet in order to wet them evenly. Then 400 gm. of Ibuprofen powder containing 5% talcum powder are sprinkled on the wetted mass of nonpareil seeds. The pellets are dried in warm air. The addition of the coating solution, coating powder and the drying procedure are repeated to apply additional coats until all the Ibuprofen powder is used up. Two final coatings are added, each coat consisting of coating solution followed by talcum powder. The pellets are thoroughly dried and screened through a No. 16 mesh screen and on a No. 30 mesh screen. The yield is approximately 100 kg.

The screened pellets are divided into three equal parts and returned to three separate coating pans and coated with coating solution followed by dusting with a mixture of stearic acid, carnauba wax and talc which work as retarding wax. The first pan is thus coated with 4 kg. of retarding wax, the second pan with 5 kg. of the retarding wax and the third with 6 kg. of retarding wax. All three parts are thoroughly dried. The release rate of each part is checked and the three parts are mixed together and again divided into two sections and returned to the coating pans.

Now the coating solution is sprayed onto each pan, followed by dusting of mixture of alginic acid and sodium carboxymethyl starch (disintegrant). This process is continued until 10% w/w of the disintegrant has been added. The pellets are thoroughly dried, and screened through a 12 mesh screen and onto a 30 mesh screen. The yield is approximately 125 kg. These pellets are then compressed on a tablet press at a weight which is equal to 1000 mg. of Ibuprofen per tablet.

These tablets are then film-coated using conventional coating techniques for improving appearance and acceptability. The coated tablets thus obtained released the active ingredient at a sustained rate over a period of six to seven hours under simulated physiological conditions.

EXAMPLE NO. 6

Potassium Chloride Granules, 40.0 kg., all passing through a No. 30 U.S. mesh screen, 90% passing through a No. 30 mesh screen, and not over 10% passing through a No. 40 U.S. mesh screen are placed in a 48-inch coating pan. The pan is set in rotation and coating solution is sprayed slowly onto the pellets in order to wet them evenly. Then 400 gm. of Potassium Chloride powder containing 5% povidone powder are sprinkled on the wetted mass of nonpareil seeds. The pellets are dried on warm air. The addition of the coating solution, and coating powder and the drying procedure are repeated to apply additional coats until all the Potassium Chloride powder is used up. Two final coatings are added, each coat consisting of coating solution followed by talcum powder. The pellets are thoroughly dried and screened through a No. 16 mesh screen and on a No. 30 mesh screen. The yield is approximately 100 kg.

The screened pellets are divided into three equal parts and returned to three separate coating pans and coated with coating solution followed by dusting with a mixture of stearic acid, carnauba wax and talc which work as retarding wax. The first pan is thus coated with 3.3 kg. of retarding wax, the second pan with 4.95 kg. of the retarding wax and the third with 6.6 kg. of retarding wax. All three parts are thoroughly dried. The release rate of each part is checked and the three parts are mixed together and again divided into two sections and returned to the coating pans.

Now the coating solution is spayed onto each pan, followed by dusting of Potassium Bicarbonate powder in one pan and citric acid, anyhdrous powder in the other. This process is continued until 10% w/w of the powder on each pan has been added. The pellets are thoroughly dried, and then screened through a 12 mesh screen and onto a 30 mesh screen. The yield is approximately 125 kg. These pellets are then compressed on a tablet press at a weight which is equal to 750 mg. of Potassium per tablet.

The tablets thus obtained released the active ingredient at a sustained rate over a period of six to seven hours under physiological conditions.

EXAMPLE NO. 7

The process of Example No. 1 is carried out replacing the mixture of corn starch and sodium starch glycolate with a mixture of methylcellulose and sodium carboxymethyl starch.

EXAMPLE NO. 8

The process of Example No. 2 is carried out replacing the mixture of alginic acid and sodium carboxymethyl starch with a mixture of potato starch and sodium carboxymethyl cellulose.

EXAMPLE NO. 9

The process of Example No. 3 is carried out replacing the potato starch and modified cellulose gum (AcDisol) with 4%, corn starch and sodium starch glycolate coated onto pellets and another 4% of the mixture added in the lubricating step, prior to compressing the tablet.

EXAMPLE NO. 10

The process of Example No. 4 is carried out replacing corn starch and cellulose powder with 5% sodium starch glycolate.

EXAMPLE NO. 11

The process of Example No. 5 is carried out replacing cornstarch and sodium starch glycolate with pregelatinized starch and plantago ovata seed husk powder.

While I have illustrated my invention with the aid of certain specific embodiments thereof, it will be readily apparent to others skilled in the art that my invention is not limited to those particular embodiments, and that various changes and modifications may be made to achieve comparable results without departing from the spirit of the invention or the scope of the appended claims.

I claim:

1. In a dense, compressed pharmaceutical tablet for oral administration which is characterized by the ability to disintegrate quickly and spontaneously into coated pellets which release medicament at a controlled rate over a period of several hours in the gastrointestinal tract, the improvement consisting essentially of a first coating of a retarding material adapted to slow the release rate of said medicament, a second thin, uniform disintegrant coating applied in a dry state on the said retardant coated pellets capable of rapidly absorbing water from the aqueous fluids of the gastrointestinal tract and disintegrating, said coated pellets adapted for compression into a dense tablet.

2. The compressed pharmaceutical tablet according to claim 1 wherein the coating of retarding material is located intermediate said medicament pellet and said disintegrant coating.

3. The compressed pharmaceutical tablet as in claim 1 in which the disintegrant agent comprises from about to about 2 percent to about 15 percent by weight of the tablet of one or more members of the group consisting of the sodium salt of carboxymethyl starch, alginic acid, corn starch, cellulose powder, potato starch, modified cellulose powder, pregelatinized starch, plantago ovata seed husk powder, sodium starch glycolate, and the sodium salt of carboxymethyl cellulose.

4. The compressed pharmaceutical tablet of claim 1 in which the disintegrant is corn starch, sodium starch glycolate or a mixture thereof.

5. The compressed pharmaceutical tablet of claim 1 wherein the disintegrant is the sodium salt of carboxymethyl cellulose.

6. The compressed pharmaceutical tablet as in claim 4 wherein the release rate of medicament in the gastrointestinal tract takes place over a period of at least four hours.

7. The compressed pharmaceutical tablet as in claim 1 wherein the disintegrant coating on approximately one-half of the pellets is the bicarbonate salt of sodium or potassium and the disintegrant coating on the remainder of the pellets is citric acid or tartaric acid or a mixture thereof.

8. The method of making a dense, compressed pharmaceutical tablet for oral administration which is characterized by the ability to disintegrate quickly and spontaneously into coated pellets which release medicament at a controlled rate over a period of several hours in the gastrointestinal tract which comprises the steps of:
   (a) applying to a seed a coating of medicament,
   (b) applying one or more coatings of a retardant material to the article produced in step (a),
   (c) thereafter applying in a dry state a disintegrant material to form a thin, uniform layer coating of a disintegrant material in an amount of about two to about fifteen percent by weight of said tablet, and
   (d) compressing a plurality of the pellets produced in step (c) into a dense pharmaceutical tablet.

9. The method of claim 8 with the added step of applying a finish film coating on said tablets.

10. The method of claim 8 in which the retardant wax material is stearic acid, carnauba wax or a mixture thereof.

11. The method of claim 8 in which the disintegrant material is corn starch, sodium starch glycolate or a mixture thereof.

12. The method of claim 8 in which the retardant material is ethyl cellulose, methyl cellulose or a mixture thereof.

13. The method of claim 8 in which the retardant material is applied as a solution or dispersion of methyl cellulose, ethyl cellulose or a mixture thereof in a solvent system of a water-ethanol mixture, an ethanol-methylene chloride mixture or a methanol-methylene chloride mixture.

14. A dense, compressed pharmaceutical tablet for oral administration comprising a plurality of medicament-containing pellets, each pellet having coated thereon a first coating of a retarding material adapted to slow the release rate of said medicament, a second thin, uniform disintegrant coating applied in a dry state on a said first coating, said disintergrant coating capable of rapidly absorbing water from aqueous fluids in the gastrointestinal tract and disintegrating, thereby dispersing said medicament-containing pellets, said coated pellets adapted for compression into a dense tablet.

15. The compressed pharmaceutical tablet according to claim 14 wherein the coating of retarding material is located intermediate said medicament pellet and said disintegrant coating.

16. The compressed pharmaceutical tablet according to claim 14 wherein said disintegrant comprises from about 2% to about 15%, by weight of the tablet, of one or more members of the group consisting of the sodium salt of carboxymethyl starch, alginic acid, corn starch, cellulose powder, potato starch, modified cellulose power, pregelatinized starch, plantago ovata seed husk powder, sodium starch glycolate, and the sodium salt of carboxymethyl cellulose.

17. The compressed pharmaceutical tablet according to claim 14 wherein the disintegrant is cornstarch, sodium starch glycolate, or a mixture thereof.

18. The compressed pharmaceutical tablet according to claim 14 wherein the disintegrant is the sodium salt of carboxymethyl cellulose.

19. The compressed pharmaceutical tablet according to claim 17 wherein the release rate of madicament in the gastrointestinal tract takes place over a period of at least 4 hours.

20. The compressed pharmaceutical tablet according to claim 14 wherein the disintegrant coating on approximately one-half of the pellets is the bicarbonate salt of sodium or potassium and the disintegrant coating on the remainder of the pellets is citric acid, tartaric acid, or a mixture thereof.

* * * * *